(12) United States Patent
Asano et al.

(10) Patent No.: US 7,462,827 B2
(45) Date of Patent: *Dec. 9, 2008

(54) NON-DESTRUCTIVE INSPECTION METHOD AND APPARATUS THEREFOR

(75) Inventors: Toshio Asano, Yokohama (JP); Kaoru Sakai, Yokohama (JP); Tetsuo Taguchi, Hitachi (JP); Isao Tanaka, Hitachi (JP)

(73) Assignee: Hitachi-GE Nuclear Energy, Ltd., Ibaraki-ken (JP)

( * ) Notice: Subject to any disclaimer, the term of this patent is extended or adjusted under 35 U.S.C. 154(b) by 457 days.

This patent is subject to a terminal disclaimer.

(21) Appl. No.: 11/204,353

(22) Filed: Aug. 16, 2005

(65) Prior Publication Data

US 2006/0033986 A1    Feb. 16, 2006

Related U.S. Application Data

(63) Continuation of application No. 09/889,920, filed as application No. PCT/JP99/01676 on Mar. 31, 1999, now Pat. No. 6,975,391.

(51) Int. Cl.
*G01N 21/88* (2006.01)
(52) U.S. Cl. .................................... 250/302
(58) Field of Classification Search ................. 250/302; 348/125
See application file for complete search history.

(56) References Cited

U.S. PATENT DOCUMENTS

| | | | |
|---|---|---|---|
| 3,774,030 A | 11/1973 | O'Connor et al. | |
| 3,988,530 A * | 10/1976 | Ikegami et al. | 348/134 |
| 4,978,862 A | 12/1990 | Silva et al. | |
| 5,412,219 A | 5/1995 | Chappelle et al. | |
| 5,494,829 A | 2/1996 | Sandstrom et al. | |
| 5,969,370 A | 10/1999 | Imaino et al. | |

(Continued)

FOREIGN PATENT DOCUMENTS

JP         58-82147        5/1983

(Continued)

OTHER PUBLICATIONS

Patent Abstracts of Japan, Publication No. 08184580, Publication Date—Jul. 16, 1996.

*Primary Examiner*—Constantine Hannaher
(74) *Attorney, Agent, or Firm*—Antonelli, Terry, Stout & Kraus, LLP.

(57) ABSTRACT

By using an image signal acquired by picking up a sample to be inspected by a color video camera, penetrant inspection and magnetic-particle inspection which are non-destructive inspections are carried out so that deficiency candidates including a pseudo deficiency are automatically detected and are displayed on a screen. A real deficiency can be detected from the deficiency candidates displayed on the screen. As image data is stored in memory means, information of a deficiency can be repeatedly reproduced on the screen. In the penetrant inspection, the chromaticity at each position on an image is acquired, a deficiency candidate is extracted based on the chrominance, and the deficiency is distinguished from a pseudo deficiency based on the differential value of the chrominance. A polarization filter is used to eliminate regular reflection originated from illumination in the penetrant inspection, and an ultraviolet-rays cutting filter is attached to the camera to prevent noise in the magnetic-particle inspection. Equipped with both a white illuminating lamp and an ultraviolet illuminating lamp, both inspections can be carried out with a single probe.

20 Claims, 22 Drawing Sheets

U.S. PATENT DOCUMENTS

| | | |
|---|---|---|
| 6,177,678 B1 | 1/2001 | Brass et al. |
| 6,525,315 B1 | 2/2003 | Motoyama |
| 6,603,126 B2 | 8/2003 | Yamada et al. |

FOREIGN PATENT DOCUMENTS

| | | |
|---|---|---|
| JP | 63-225153 | 9/1988 |
| JP | 1-109249 | 4/1989 |
| JP | 1-212339 | 8/1989 |
| JP | 3-181807 | 8/1991 |
| JP | 4-12258 | 1/1992 |
| JP | 4-223262 | 8/1992 |
| JP | 5-107202 | 4/1993 |
| JP | 6-50941 | 2/1994 |
| JP | 6-118062 | 4/1994 |
| JP | 6-300739 | 10/1994 |
| JP | 8-2601 | 1/1996 |
| JP | 08-184580 | 7/1996 |
| JP | 10-300688 | 11/1998 |
| WO | WO 9844336 A1 * | 10/1998 |

* cited by examiner

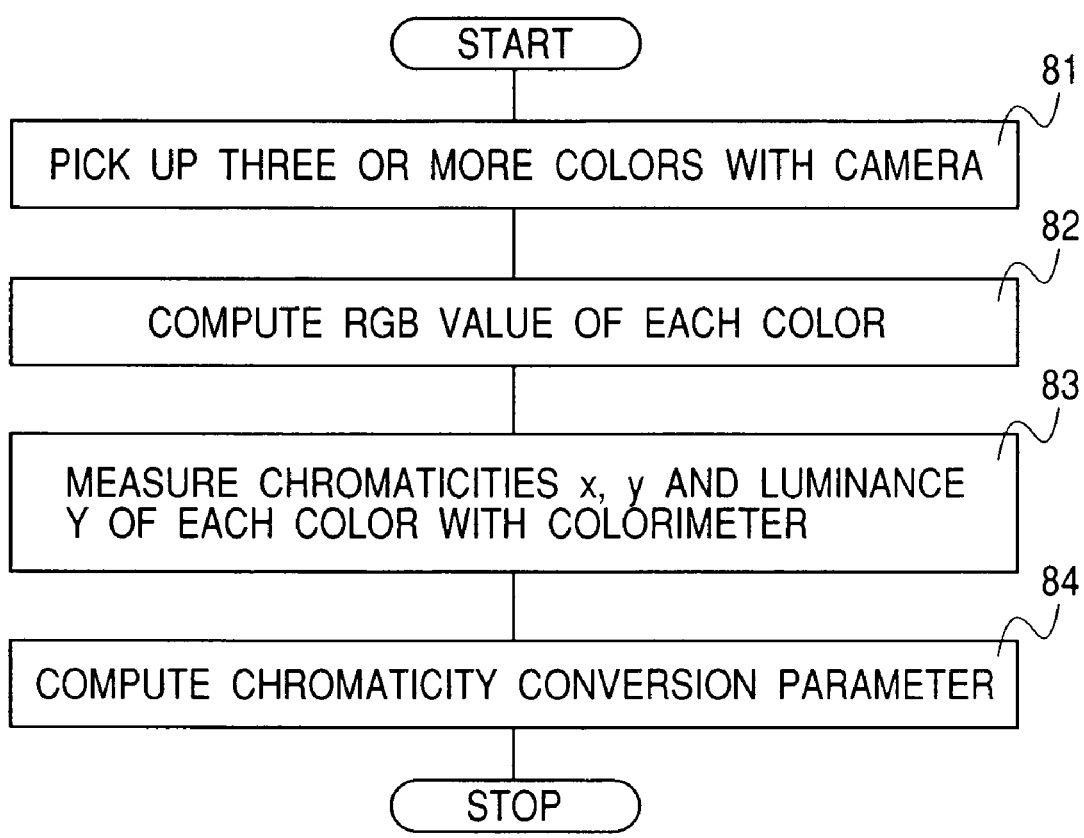

FIG. 10
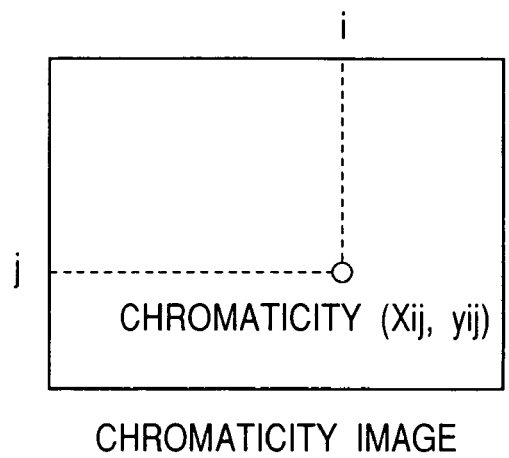
CHROMATICITY IMAGE
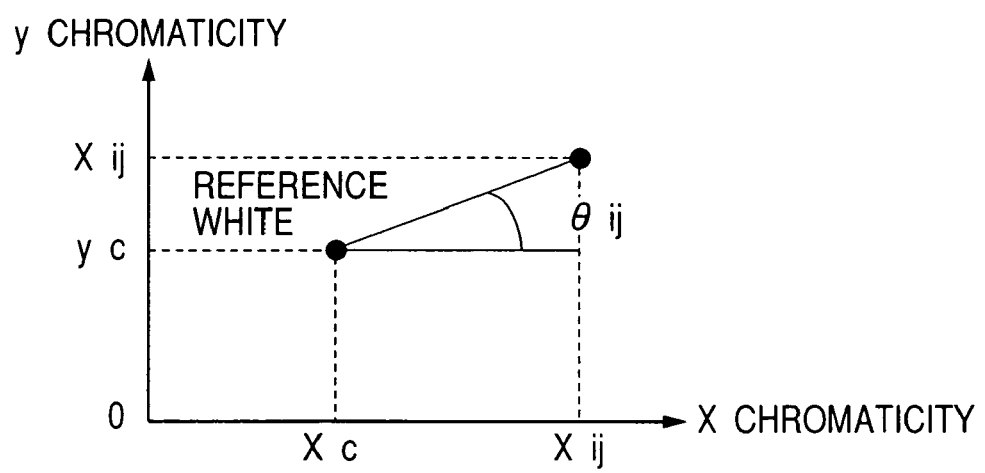
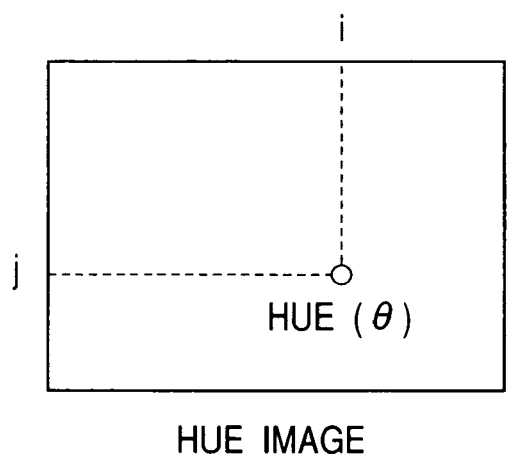
HUE IMAGE

FIG. 11
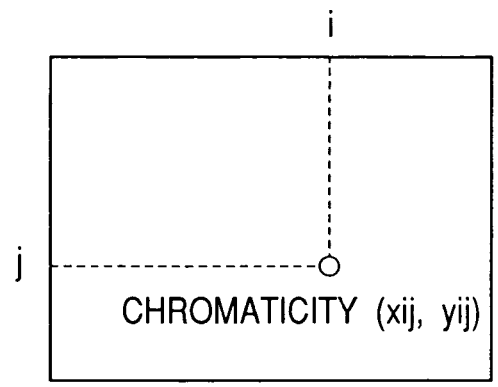
CHROMATICITY IMAGE
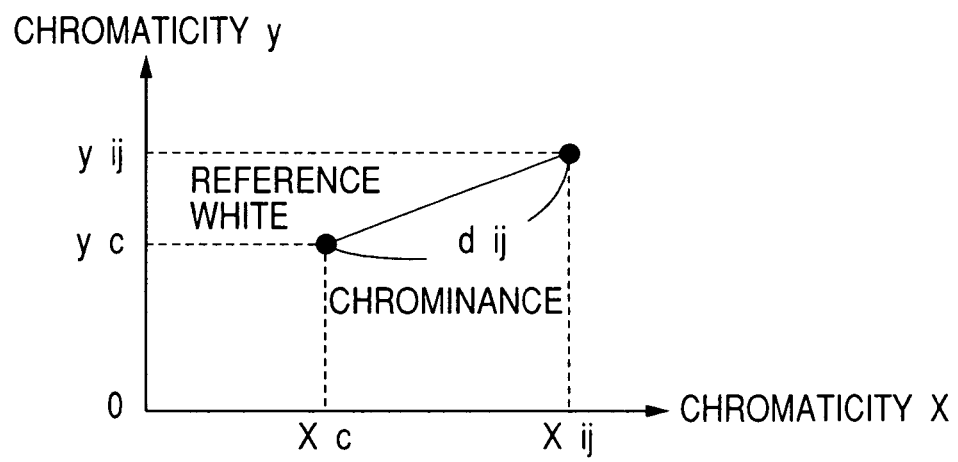
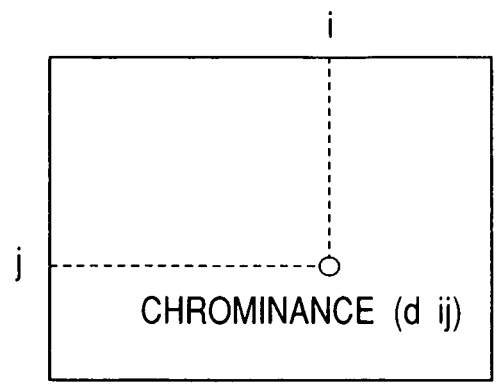
CHROMINANCE IMAGE

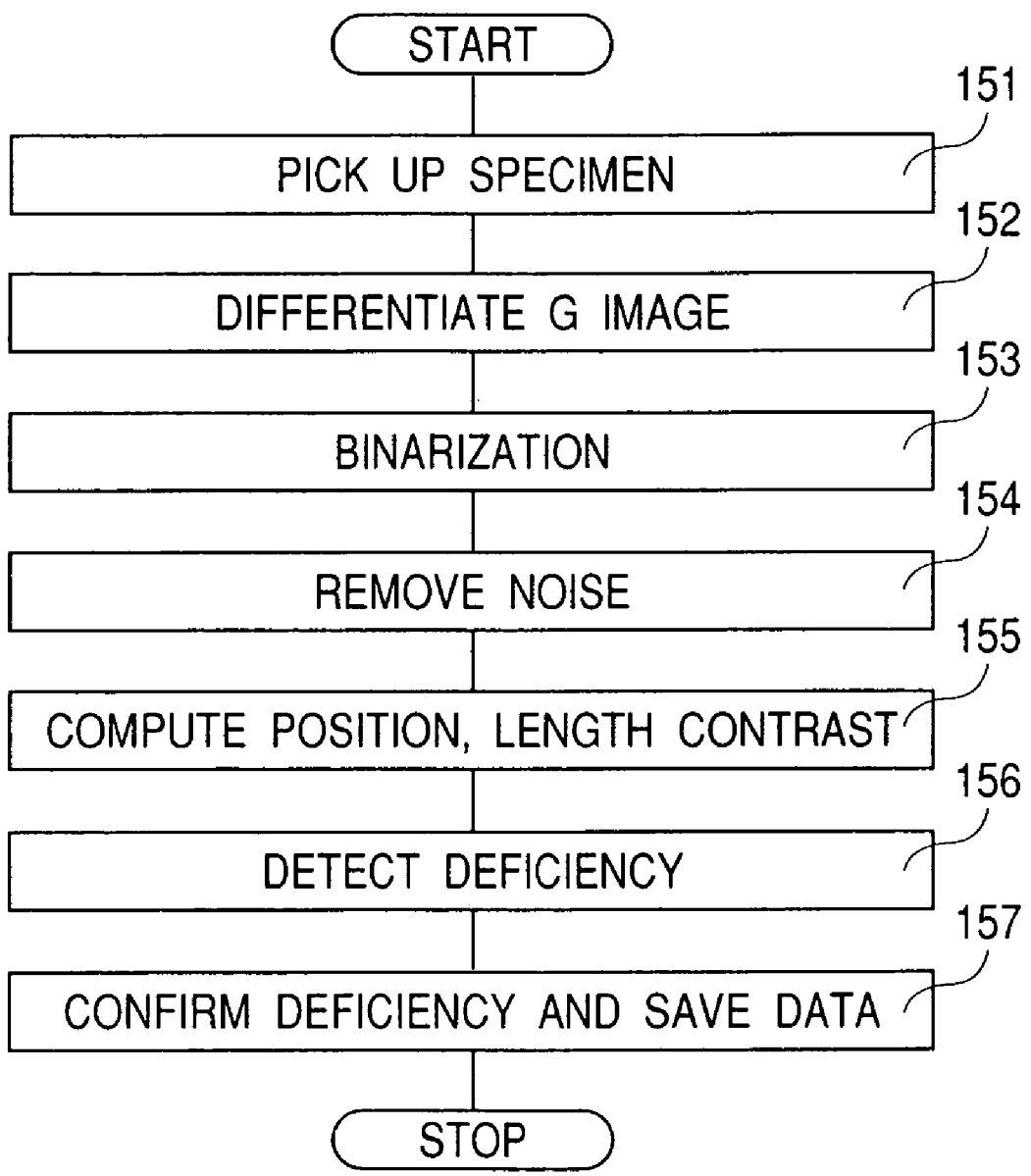

NON-DESTRUCTIVE INSPECTION METHOD AND APPARATUS THEREFOR

CROSS-REFERENCE TO RELATED APPLICATIONS

This is a continuation of application Ser. No. 09/889,920 filed Jul. 25, 2001 now U.S. Pat. No. 6,975,391, which is the national phase application from international application No. PCT/JP99/01676 filed on Mar. 31, 1999, the entire contents of all of which, as originally filed and also as made of record, is incorporated herein by reference.

TECHNICAL FIELD

The present invention relates to a method of inspecting a deficiency, such as a crack in a metal surface, and, more particularly, to an inspection method for performing non-destructive inspections called penetrant inspection and magnetic-particle inspection and an apparatus therefor.

BACKGROUND ART

A penetrant inspection and magnetic-particle inspection inspect a deficiency, such as a crack (crack) having an opening in the surface of metal in a non-destructive manner. In the penetrant inspection, normally, a red liquid called penetrant is applied to the surface to be inspected, the penetrant is wiped out after a predetermined time passes, and white powder called a developer is applied. If there is a deficiency, such as a crack, the penetrant remaining in the crack comes to the surface due to capillary phenomenon, indicating a deficiency in red. In case of magnetic-particle inspection, a solution containing fluorescent magnetic powder is sprayed on a specimen or a magnetic substance to magnetize the specimen. If there is a deficiency, such as a crack, the magnetic flux is concentrated on the deficient portion, so that the fluorescent magnetic powder is gathered and emits green light when ultraviolet rays are irradiated, thereby showing a deficiency. Conventionally, those deficiency indications are observed visually to inspect deficiencies.

Such a visual inspection has a problem on the inspection reliability, such as missing of a deficiency due to the fatigue of an inspector or that different inspection results due to the difference in capability among inspectors are left merely by characters, such as "passed".

With regard to the magnetic-particle inspection, an automatic inspection apparatus has been developed for those parts which are important and are to be mass-produced. As it is a special-purpose apparatus, it cannot easily inspect parts having multifarious shapes.

Further, as the penetrant inspection needs to detect surface colors as a two-dimensional distribution at high precision, even if there is a calorimeter capable of accurately measuring the chromaticity at a point, two-dimensional sweeping is needed. In terms of inspection time and cost, therefore, it is difficult to easily perform automatic inspection of parts having multifarious shapes.

Furthermore, when a specimen was large, there were cases where it could not tell what part of the specimen the image that was acquired by automatic inspection was or what part of the specimen the detected deficiency was.

Moreover, if both the penetrant inspection and magnetic-particle inspection can be done automatically by a single apparatus, the economical merit would be improved significantly, but such an apparatus and technology have not yet appeared so far.

It is therefore an object of the invention to provide a deficiency inspection method, a deficiency inspection apparatus and a deficiency-inspection aiding method which overcome the above-described problems and facilitate discrimination of real deficiencies.

It is also an object of the invention to provide a deficiency inspection method, a deficiency inspection apparatus and a deficiency-inspection aiding method which can easily find the position of a deficiency even on a large specimen.

DISCLOSURE OF INVENTION

The invention picks up a specimen using a color video camera. If a color video camera is used directly, however, it cannot pickup an image properly in the penetrant inspection because of the irradiation-oriented regular reflection light from the specimen. In the magnetic-particle inspection, illumination light (ultraviolet rays) causes a foreign matter on the specimen to emit blue light, making it difficult to identify a deficiency. To eliminate the regular reflection light, therefore, a polarization filter is put in both the illumination and the camera. Further, a filter for cutting ultraviolet rays is placed in front of the camera.

As the color camera, a white illuminating lamp and an ultraviolet illuminating lamp are constructed as a single probe, it can be used both in the penetrant inspection and magnetic-particle inspection. In the penetrant inspection, xy chromaticities on the surface of the specimen are computed from a video signal from the color video camera to detect a red deficiency-indicating portion. In the magnetic-particle inspection, detection is made after differentiation is performed on a green video signal to highlight a deficiency.

To prevent overlooking and overdetection in automatic inspection, the inspection result is displayed in a color image and portions that have been determined as deficiencies in the automatic inspection are encircled in rectangular shapes so that an inspector checks the rectangular portions against the original images one by one to discriminate if they are real deficiencies. The original images and the inspection results are saved as recordings on a magneto-optical disk or the like.

When a specimen is like an elongated object which cannot be fitted in one field of view, the inspection position is specified by placing a scale in the pickup field of view and simultaneously picking up the scale and an image to be inspected.

BRIEF DESCRIPTION OF DRAWINGS

FIG. 8 is a diagram showing the flow of a camera calibration process.

FIG. 10 is a diagram for explaining a method of computing a hue on a chromaticity diagram, FIG. 11 is a diagram for explaining a method of computing a chrominance on the chromaticity diagram.

FIG. 15 is a diagram showing an example of an image processing algorithm in the magnetic-particle inspection of the invention.

BEST MODE FOR CARRYING OUT THE INVENTION

A preferred embodiment of the invention will now be described with reference to the accompanying drawings.

FIG. 1 shows one example of a deficiency which is inspected in the invention.

Figure 1A:
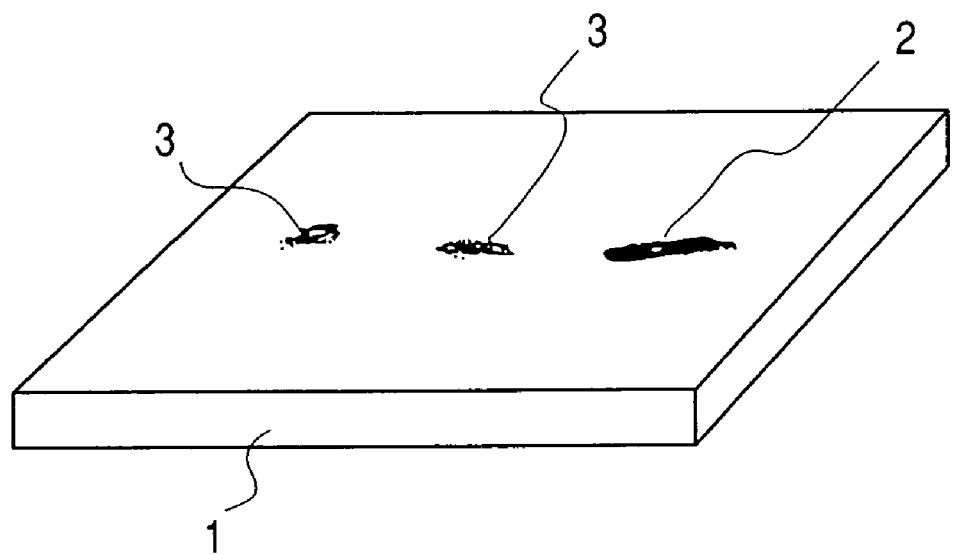
FIGS. 1A and 1B are diagrams showing examples of inspection targets which are handled in the invention.

FIG. 1A shows one example of a penetrant inspection image, a white penetrant is applied to a specimen 1, a deficiency 2 (high contrast) and pseudo deficiencies 3 (low contrast) are observed. In the penetrant inspection, the deficiency 2 is highlighted as a red indicated pattern. The pseudo deficiencies appear when the penetrant stays in surface-polishing originated lines or the like and cannot be wiped out clean, and becomes a light red indicated pattern.

Figure 1B:
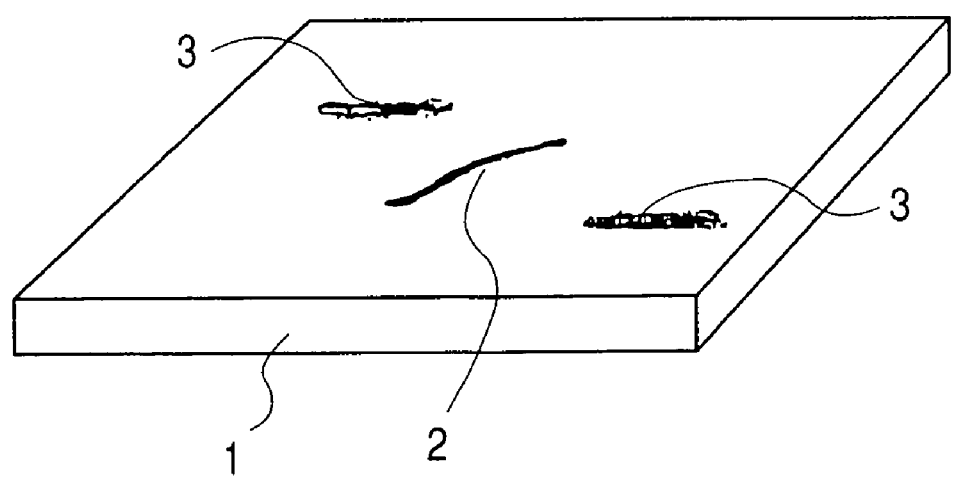

FIG. 1B shows one example of a magnetic-particle inspection image, and it is assumed that a deficiency 2 exists on a specimen and fluorescent magnetic powder has already been applied and magnetized. When ultraviolet rays are illuminated on it, the fluorescent magnetic powder that has gathered on the deficiency 2 due to magnetization emits green light. If there is a welded portion in the specimen 1, for example, the fluorescent magnetic powder is gathered along welding beads so that green pseudo deficiencies 3 appear in some cases.

Figure 2:
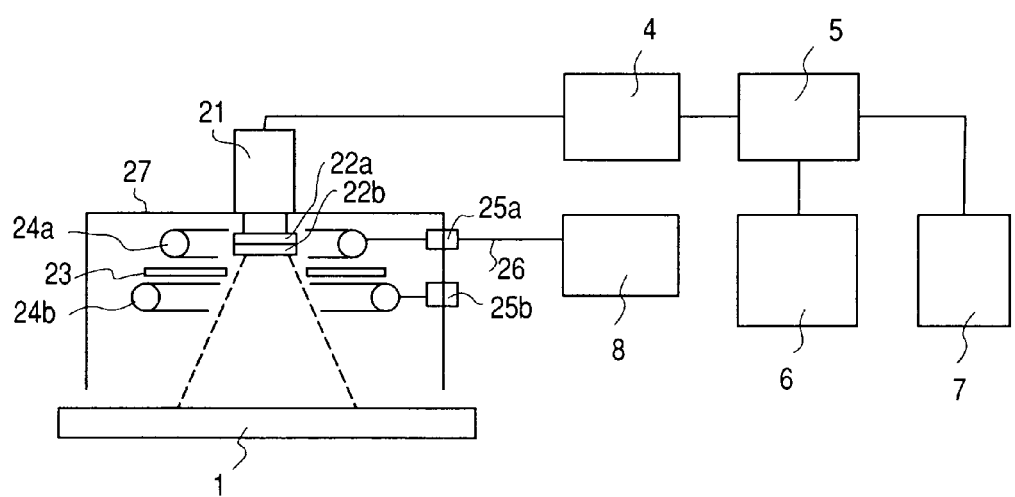
FIG. 2 is a structural diagram of a deficiency inspection apparatus showing one embodiment of the invention.

FIG. 2 is a structural diagram of a deficiency inspection apparatus according to the invention. There are a deficiency 2 and pseudo deficiencies 3 on a specimen 1. They are picked up by a color video camera 21. A white illuminating lamp 24a is turned on in inspecting a penetrant inspection image, whereas an ultraviolet illuminating lamp 24b is turned on in the magnetic-particle test. The white illuminating lamp 24a is connected to a white-illuminating-lamp connector 25a and is connected to an illumination power supply 8 by an illumination cable 26.

In the magnetic-particle inspection, the illumination cable 26 is connected to an ultraviolet-illuminating-lamp connector 25b. To avoid the influence of outside light, a hood 27 is attached. Although the illuminating lamp in use has a ring shape in FIG. 2, a single rod-shaped lamp or plural rod-shaped lamps may be used.

A color video signal from the color video camera 21 includes a type in which R, G and B are separated and a composite video signal. Either signal is stored as image data for R, G and B in a color image memory 4. The color image data is analyzed by a computer 5 and the results of deficiency detection are shown on a color monitor 6.

The deficiency inspection results are saved in a data memory device 7. Further, an image displayed on the color monitor 6 can be printed out from an unillustrated printer as needed.

A polarization filter 22a and an ultraviolet-rays cutting filter 22b are placed in front of the lens of the color video camera 21. A polarization filter plate 23 is provided under the white illuminating lamp 24a. The polarization filter 22a and the polarization filter plate 23 serve to prevent reflection of the illumination or regular reflection light from the specimen 1 in the inspection of the penetrant inspection image. While the output video image of the color video camera 21 is watched, the polarization filter 22a is turned and is fixed to the place where there is least image reflection or light reflection. The adjustment of the polarization filter 22a may be done automatically based on the video output signal of the color video camera 21.

The ultraviolet-rays cutting filter 22b serves to inhibit unnecessary light emission from an adhered foreign matter caused by the ultraviolet illuminating lamp 24b.

FIG. 3 is a diagram showing the effects of the polarization filter 22a and the polarization filter plate 23.

Figure 3A:
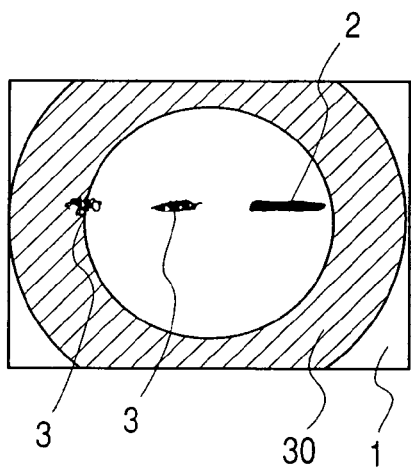
FIGS. 3A and 3B are diagrams showing the effects of a polarization filter in the apparatus structure in FIG. 2, and FIGS. 4A and 4B are diagrams showing the effects of an ultraviolet-rays cutting filter.
Figure 3B:
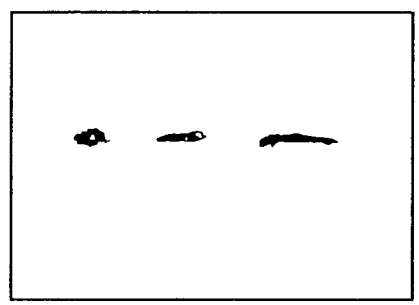

FIG. 3A shows a state where there are no filters, and FIG. 3B shows a state where the filters are attached and the rotational angles of the filters are adjusted. In FIG. 3A, there is an illumination reflection 30, making deficiency detection difficult. The ring-like illumination reflection is on the assumption of a case where the white illuminating lamp 24a is ring-like. In FIG. 3B, this illumination reflection is gone.

Figure 4A:
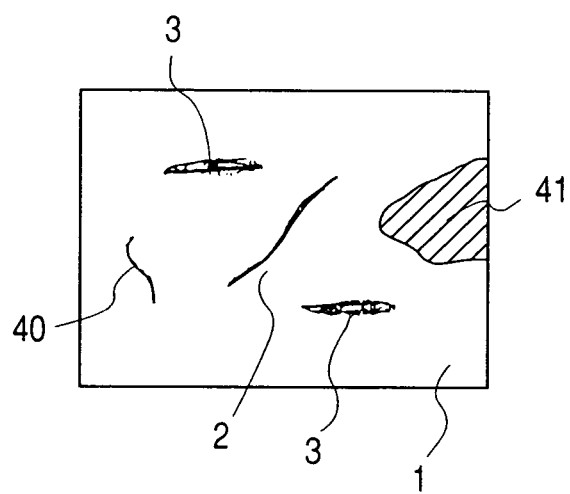
Figure 4B:
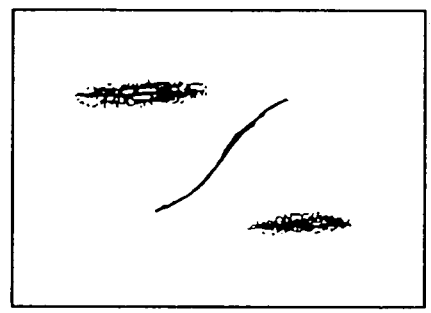

FIG. 4 is a diagram showing the effects of the ultraviolet-rays cutting filter 22b. FIG. 4A shows a state where there are no filters, and FIG. 4B shows a state where the filters are attached. In FIG. 4A, light emission from a foreign matter 40, such as a little piece of thread, and regular reflection light 41 from the specimen are picked up by the color video camera 21, making deficiency detection difficult. In FIG. 4B, those noises are cut and the image shows only light emission by the fluorescent magnetic powder as in a case where the specimen 1 is visually observed by a man.

Figure 5:
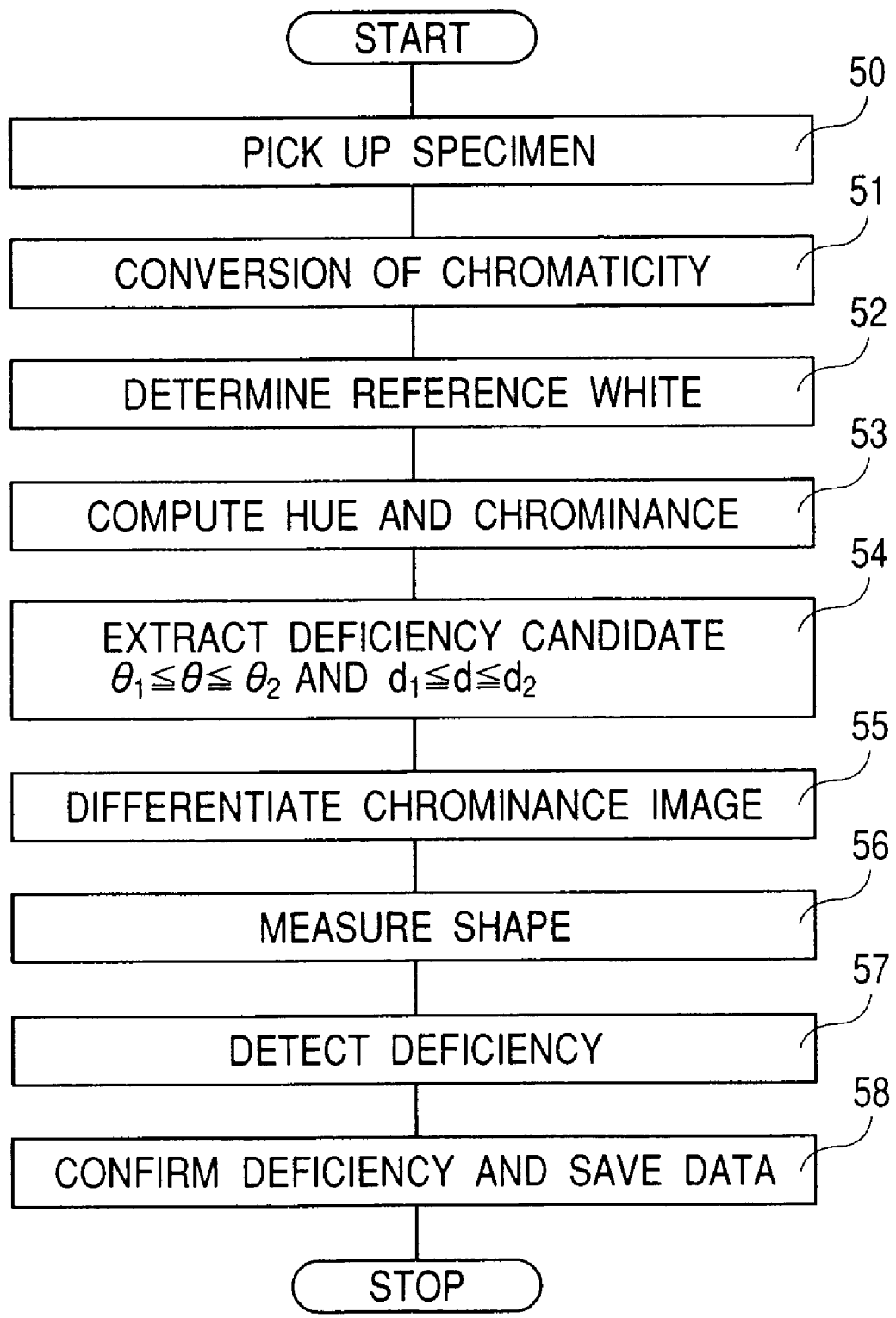
FIG. 5 is a flowchart illustrating the flow of an automatic inspection method in a penetrant inspection according to the invention.

To begin with, a method of detecting a crack deficiency in a penetrant inspection image will be explained with reference to FIGS. 5 through 13. FIG. 5 illustrates a method of automatically detecting the deficiency 2 in the penetrant inspection.

First, image pickup 50 of the specimen 1 on which a developer is applied is executed using the white illuminating lamp 24a. Next, chromaticity conversion 51 to acquire xy chromaticity values of individual pixels from acquired R, G and B color image data is executed.

Next, determination 52 of reference white to compute the reference white chromaticity of the developer is performed and computation 53 of the hue and chrominance at each position on the image with respect to the reference white is carried out.

Then, a region whose hue and chrominance lie within a specific range is extracted by binarization in order to execute extraction 54 of deficiency candidates.

A real deficiency 2 has a clear contour portion, and a pseudo deficiency often has an unclear contour portion. In this respect, differentiation 55 of the chrominance image is performed and the ratio of a change in chrominance of the contour portion of the extracted deficiency candidate area is obtained. Next, shape measuring 56 for the area, the aspect ratio, the length and so forth of the deficiency candidate area is performed. Then, a region whose ratio of a change in chrominance and whose length and area are larger than specified ones is detected as the real deficiency 2 in detection 57 of deficiency. Further, the inspection results are displayed on the color monitor 6 and a deficiency is confirmed by an inspector, after which image data, shape data, positional information, etc. are saved in the data memory device 7 or printed out to be saved as a hardcopy 58.

Figure 6:
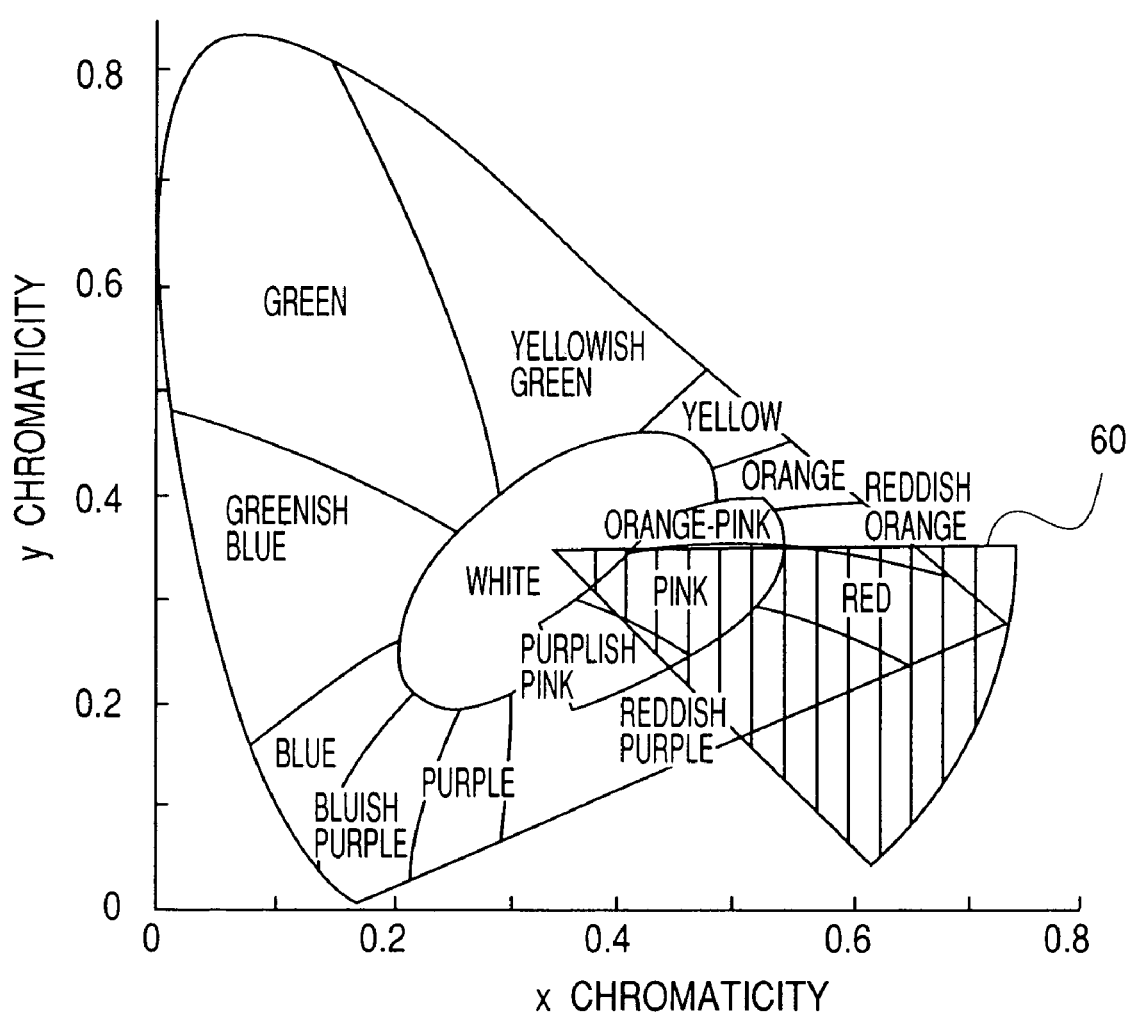
FIG. 6 shows an xy chromaticity diagram.

In color-based inspection, it is necessary to evaluate colors quantitatively. In the step of chrominance conversion 51, therefore, RGB data of the picked-up color image is converted to chromaticities x, y and luminance Y that are specified by CIE (Commission internationale de l'éclairage), and inspection is carried out using them. Expression of chromaticities x, y in two-dimensional orthogonal coordinates is called a chromaticity diagram shown in FIG. 6. In the chromaticity diagram, individual colors are arranged around white and become clearer as they are located farther away from white. Hereinafter, the tone is called a hue, the clearness of each color is called a chromaticness and the distance between two chromaticities on the chromaticity diagram is called a chrominance. FIG. 6 shows a chromaticity range of a penetrant inspection image.

Figure 7:
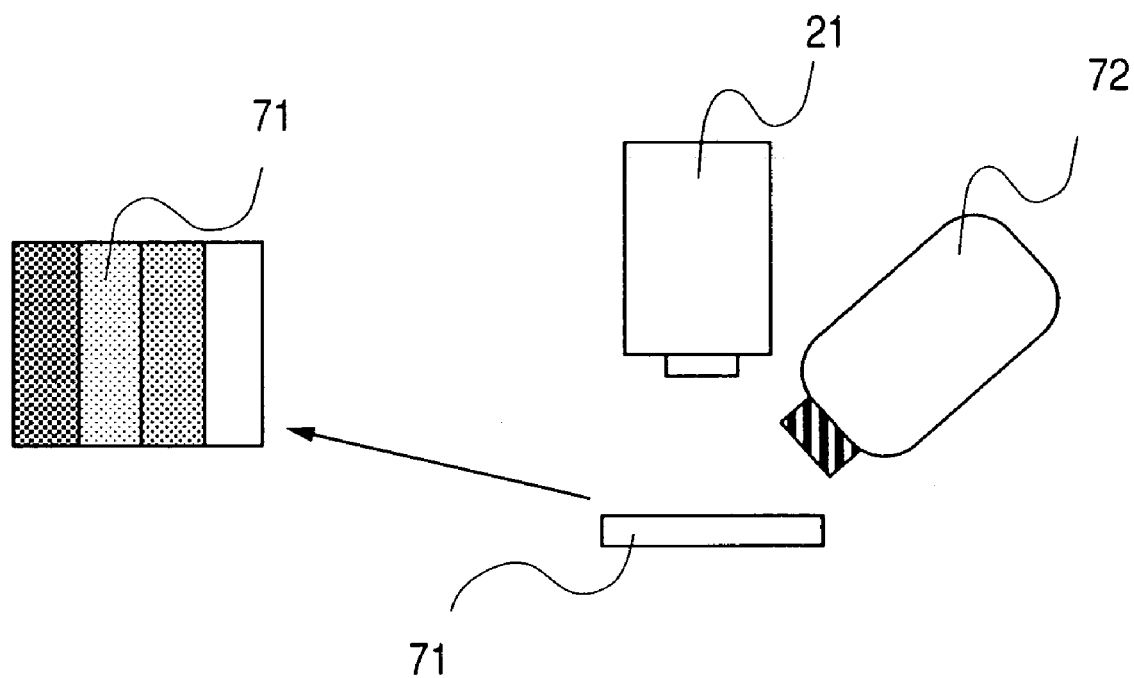
FIG. 7 is a diagram showing a structure for camera calibration.

In this method, color calibration is executed beforehand using a camera calibration color card 71 as shown in FIG. 7 in order to perform high-precision conversion of RGB data to chromaticities x, y and luminance Y. The flow of that process is shown in FIG. 8. The camera calibration color card 71 has three or more colors painted. The colors are picked up by the color video camera 21 (81), and the RGB values of the individual colors are computed (82). The chromaticities x, y and luminance Y are measured (83) by a calorimeter 72. The relationship between the RGB values and xyY values is expressed by equations (1) and equation (2).

$$\begin{pmatrix} X \\ Y \\ Z \end{pmatrix} = \begin{pmatrix} a_{11} & a_{12} & a_{13} \\ a_{21} & a_{22} & a_{23} \\ a_{31} & a_{32} & a_{33} \end{pmatrix} \begin{pmatrix} R \\ B \\ G \end{pmatrix} \quad (1)$$

where X, Y and Z are called three stimulus values.

$$\text{chromaticity: } x = \frac{X}{X+Y+Z}, \quad y = \frac{Y}{X+Y+Z} \quad (2)$$

$$\text{luminance: } Y$$

The xyY values are computed by substituting the RGB values of the RGB values of the individual colors acquired from the camera into the equations (1) and (2) and conversion parameters specific to the camera are obtained by acquiring $a_{11}$ to $a_{33}$ which make the values coincide with the xyY values measured by the calorimeter. As there are nine unknown parameters, the parameters can be computed from the RGB values $(R_1, G_1, B_1)$ to $(R_3, G_3, B_3)$ of at least three colors and their corresponding xyz values $(x_1, y_1, Y_1)$ to $(X_3, y_3, Y_3)$ from the colorimeter.

As it is apparent from the equation (2) that XYZ can be computed from the xyY values from the following equation (3), $$X = Y \times x/y, \quad Y = Y, \quad Z = Y \times (1-x-y)/y \quad (3)$$

XYZ are acquired by substituting the xyY values of the three colors from the colorimeter into the equation (3) and are substituted into the equation (1).

$$\begin{pmatrix} X_i \\ Y_i \\ Z_i \end{pmatrix} = \begin{pmatrix} a_{11} & a_{12} & a_{13} \\ a_{21} & a_{22} & a_{23} \\ a_{31} & a_{32} & a_{33} \end{pmatrix} \begin{pmatrix} R_i \\ B_i \\ G_i \end{pmatrix} \quad (i=1,2,3) \quad (4)$$

Accordingly, it is possible to acquire conversion parameters $a_{11}$ to $a_{33}$ specific to the camera (84) and acquire, from the RGB values from the camera, the xyY values that are equal to the values from the colorimeter.

Figure 9A:
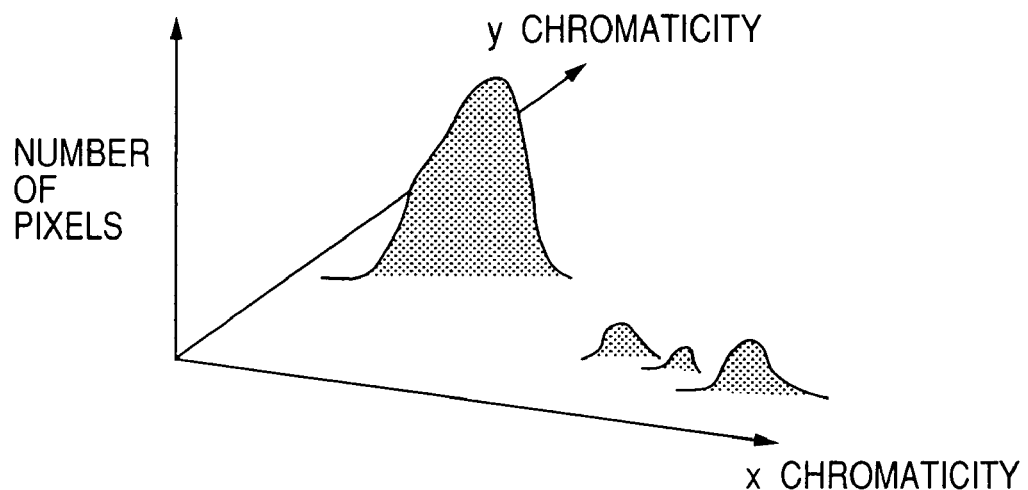
FIGS. 9A-C are diagrams illustrating a method of acquiring a reference white chromaticity from a chrominance image.
Figure 9B:
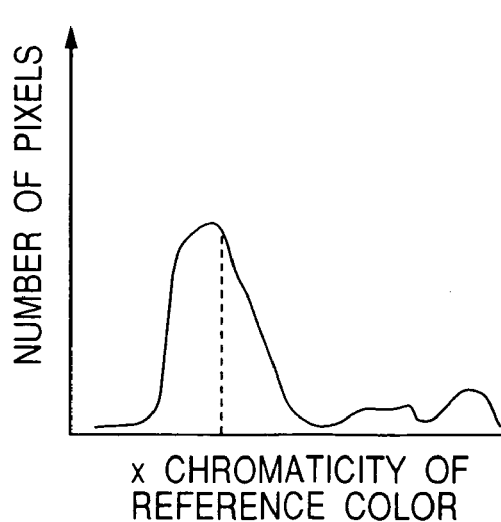
Figure 9C:
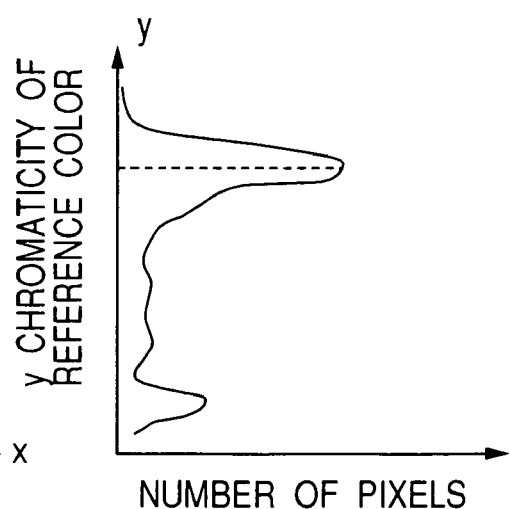
Figure 12:
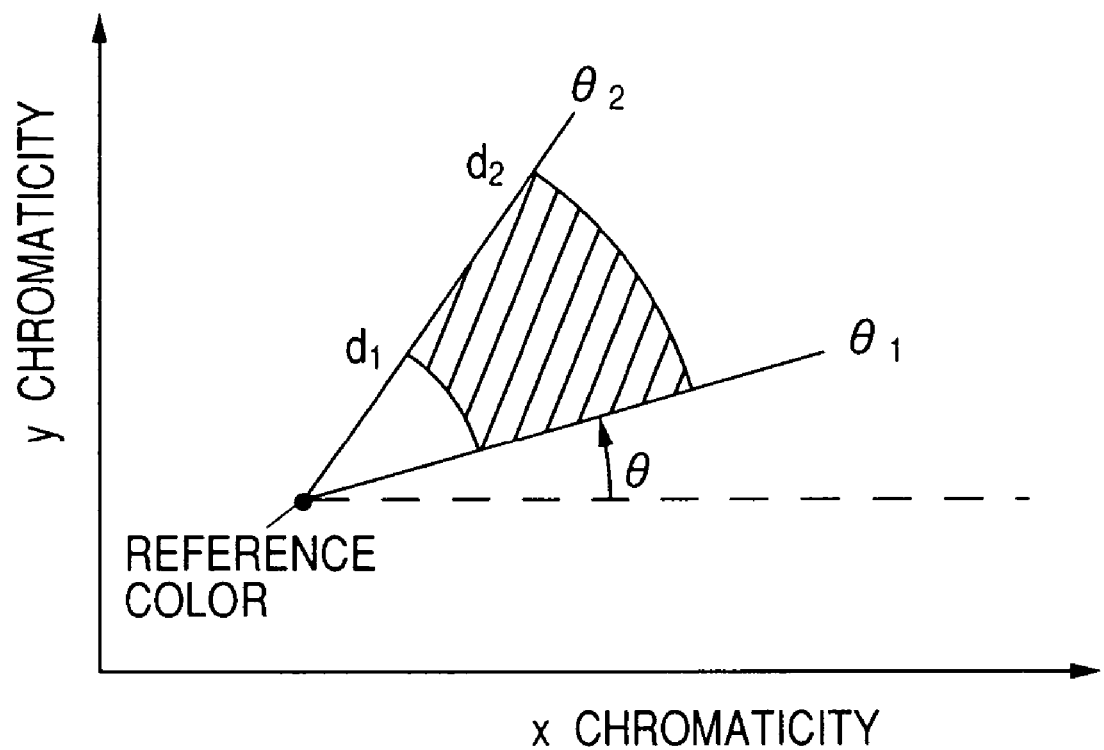
FIG. 12 is a diagram illustrating a method of acquiring a deficiency candidate area from the hue obtained in FIG. 10 and the chrominance obtained in FIG. 11, and FIGS. 13A-D are diagrams illustrating a method of acquiring a deficiency area by discriminating a pseudo deficiency from the deficiency candidate area obtained in FIG. 12.

Using the conversion parameters specific to the camera that have been computed beforehand by calibration, the RGB values acquired from the camera are subjected to chromaticity conversion to xyY values and a chromaticity distribution in the image is computed, after which the chromaticity value of the developer or the chromaticity of a non-deficient portion in the image is computed as a reference value in 52. First, the chromaticities x, y of each pixel in the image are checked and the number of pixels that take x, y values as given in a graph in FIG. 9A is counted to prepare the two-dimensional chromaticity distribution of the chromaticities. Then, the x chromaticity value (FIG. 9B) and the y chromaticity value (FIG. 9C) for which there are the largest number of pixels in the image are acquired. As most of the image is a non-deficient portion, the x, y chromaticity values at the peak values in the two-dimensional chromaticity distribution become xy chromaticity values of the reference white.

In 53, the hue and chrominance at each position on the image with respect to the reference white are computed. Given that the chromaticity of the reference white is $(x_c, y_c)$ and the chromaticity at the position (i, j) on the image is $(x_{ij}, y_{ij})$, the hue at the position (i, j) is computed in the direction toward the reference color on the chromaticity diagram as shown in FIG. 10. The computation equation is given in an equation (5).

$$\text{hue: } \theta_{ij}\left(\frac{y_{ij}-y_c}{x_{ij}-x_c}\right) \quad (5)$$

Further, the chrominance at the position (i, j) is computed in terms of a distance from the reference color on the chromaticity diagram as shown in FIG. 11. The computation equation is given in an equation (6).

$$\text{chrominance: } d_{ij} = \sqrt{(x_{ij}-x_c)^2 + (y_{ij}-y_c)^2} \quad (6)$$

From the hue and chrominance at each position of the image with respect to the reference white computed in the above-described manner, the range that is wanted to be detected as a deficiency is limited by the hue (in the diagram, the range of the hue θ is $\theta_1 \leq \theta \leq \theta_2$), and the degree of a difference in clearness of the color and the reference white is limited by the chrominance (in the diagram, the range of the chrominance d is $d_1 \leq d \leq d_2$). And, portions which lie within this range are extracted as deficiency candidate areas.

Some of the deficiency candidates that have been acquired through the limitation with the hue and chrominance may not be needed to be detected as deficiencies. For example, a portion whose chromaticity gradually changes with respect to the reference white is not a deficiency, but an area which has a clear contour is a deficiency. Therefore, a portion whose color changes gently with respect to the ambient colors is considered as a normal portion or pseudo deficiency 3, and a portion whose color changes sharply is considered as a deficiency 2. In (55), the amounts of a change in chrominance with respect to the reference white are acquired for deficiency candidate areas and only the area whose value is equal to or greater than a given value is considered as a deficiency.

Figure 13A:
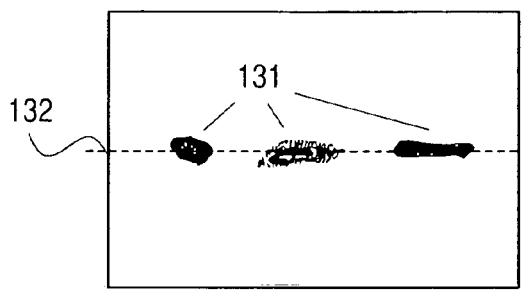
Figure 13C:
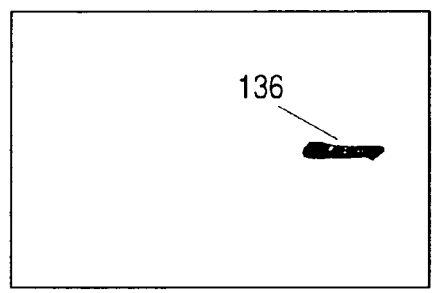
Figure 13B:
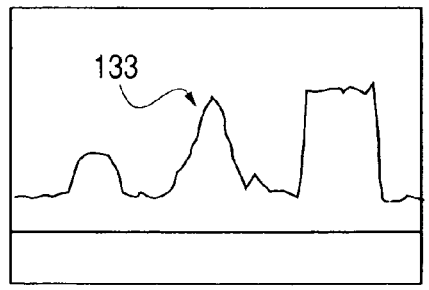
Figure 13D:

A description will be given with reference to FIG. 13. FIG. 13A shows deficiency candidate areas 131 extracted in 54. 133 in FIG. 13B is a graph of chrominance with respect to the reference white on 132 in FIG. 13A. Further, the amount of a change in the chrominance 133 at each position on 132 or differentiation of 133 is a chrominance differentiation distribution 134 in FIG. 13D. Apparently, an area which has a small amount of a change in chrominance with respect to the reference white has a small differential value. As indicated in (d), an area whose differential value is larger than a given value 135 is considered as a deficiency area. As a result, only a deficiency area 136 which has a large chrominance and has a large amount of a change in chrominance or has a clear contour as in FIG. 13C is detected.

Figure 14A:
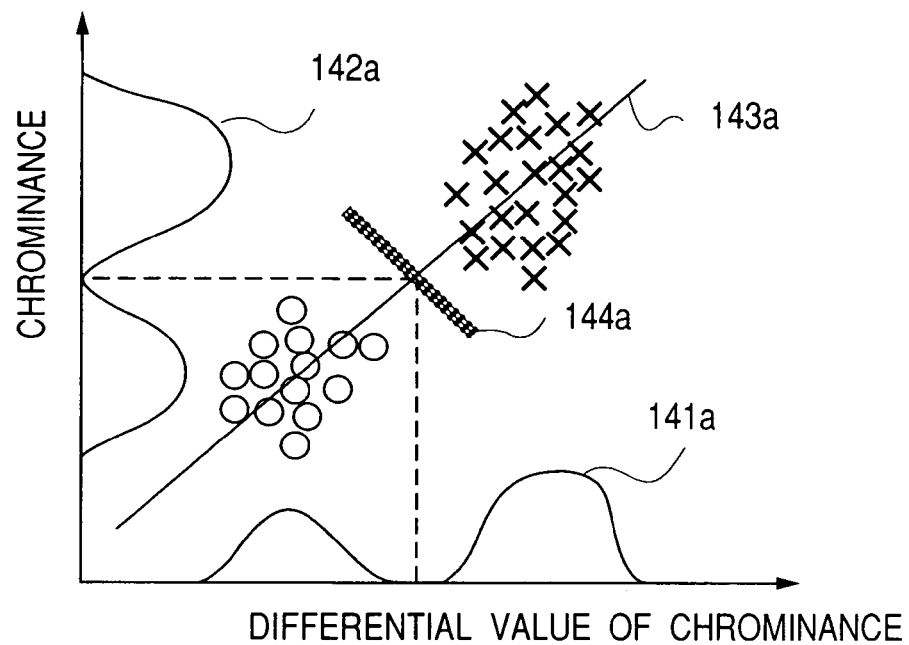
FIGS. 14A and 14B are diagrams for explaining a method of acquiring a threshold value 135 to acquire a deficiency area by discriminating a pseudo deficiency from the deficiency candidate area shown in FIG. 13.
Figure 14B:
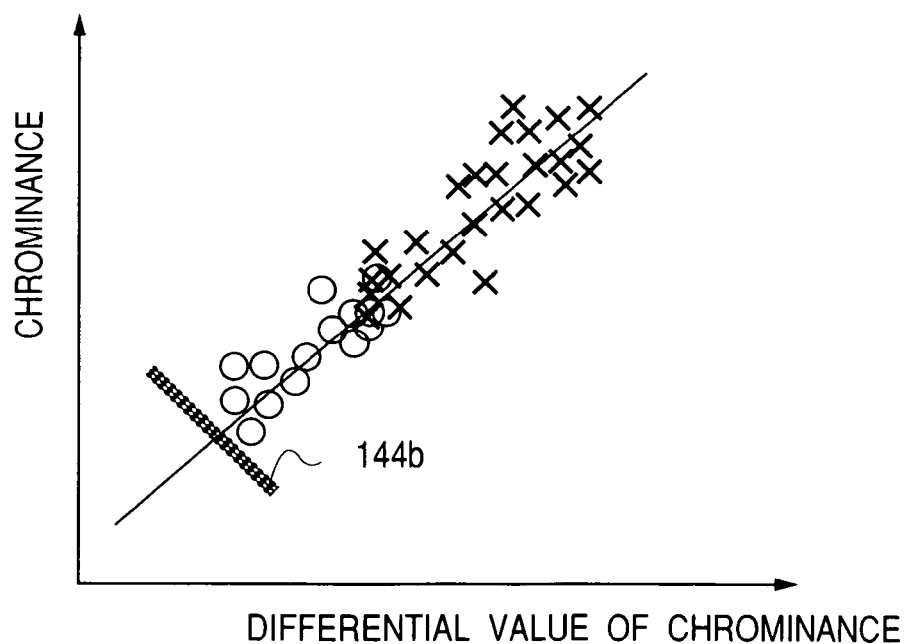
Figure 16A:
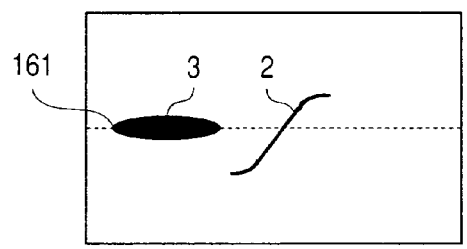
FIGS. 16A-D are diagrams for explaining a method of discriminating a pseudo deficiency in the magnetic-particle inspection of the invention.
Figure 16C:
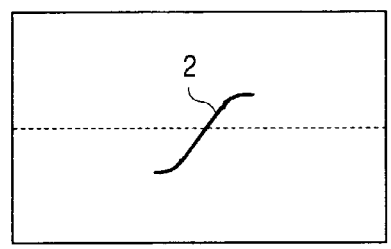
Figure 16B:
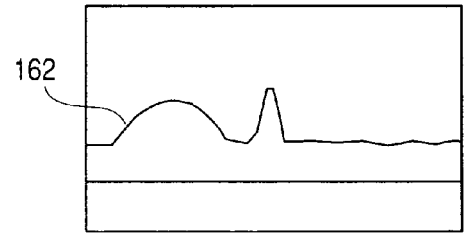
Figure 16D:
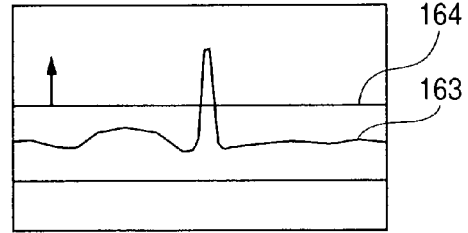

A method of determining the threshold value 135 will now be discussed with reference to FIG. 14. In a graph in FIG. 14A, the vertical axis is the maximum value in the chrominances in each deficiency candidate area extracted by the hue and chrominance, the horizontal axis is the maximum value in the differential values of the chrominance at the contour portion of each deficiency candidate area, and the values for the real deficiency 2 are plotted by X and the values for the pseudo deficiency 3 are plotted by ○. 141a is a degree distribution of the individual chrominance differential values and 142a is a degree distribution of the chrominance values. When a deficiency is clearly distinguished from a pseudo deficiency, a decision line 144a should be a straight line 144a that passes the bottom peaks in the degree distributions 141a and 142a and is perpendicular to a main axis 143a of inertia at the plotted points. When a deficiency is not distinguished from a pseudo deficiency, a decision line should be 144b as shown in FIG. 14B. That is, all deficiency candidate areas are detected as deficiencies to avoid any overlooking and missing.

A deficiency detection method in the magnetic-particle inspection will now be described using FIGS. 15 and 16.

FIG. 15 shows an example of an image processing algorithm to analyze the contents of the data memory device 7 in the magnetic-particle inspection. Acquisition of an RGB image is performed (151), then differentiation of a G image which contains the largest amount of emission information of the fluorescent magnetic powder is performed (152). This highlights a portion, such as a crack deficiency, which has a large linear change in luminance Y, and does not highlight a portion, such as a portion where magnetic powder stays, which has a high luminance but has a small change in luminance.

Next, a threshold value for binarization is determined from the average value of the G differential image and binarization is performed (153). An image noise, such as an isolated point, is removed from the binarized image (154), then deficiency candidates are acquired, after which the lengths, contrasts and so forth of those deficiency candidates are computed (155). When those values are larger than specified values, they are determined as deficiencies.

FIG. 16 shows a method of discriminating a deficiency from a pseudo deficiency. When the luminance distributions of the deficiency 2 and the pseudo deficiency 3 are taken on a line 161 as shown in FIG. 16A, for example, a luminance distribution 162 as shown in FIG. 16B is acquired. The luminance values of the deficiency 2 and the pseudo deficiency 3 are about the same. Differentiating the luminance distribution 162 yields a luminance differential distribution 163 as shown in FIG. 16B. As the luminance of the deficiency 2 changes drastically and the luminance of the pseudo deficiency 3 changes slowly, only the deficiency 2 can be extracted as in FIG. 16C by determining the results of the differentiation using a decision threshold value 164 of FIG. 16D.

Figure 17:
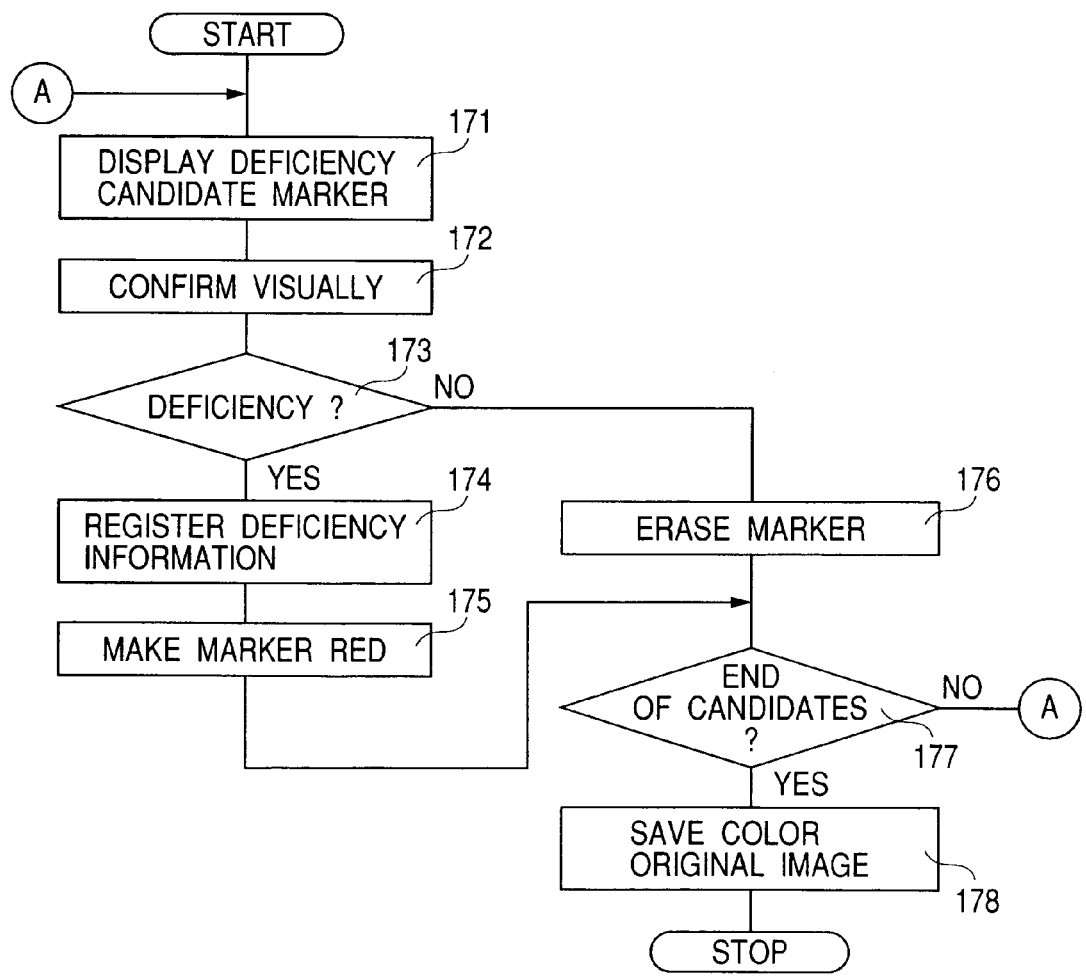
FIG. 17 is a flowchart illustrating the process of confirming a deficiency and saving data in the invention.

With reference to FIG. 17, confirmation of a deficiency and data saving will be explained. Although a deficiency should have been distinguished from a pseudo deficiency and only a deficiency should have been extracted, visual confirmation of a deficiency is executed last in both the penetrant inspection and the magnetic-particle inspection in order to prevent missing or erroneous determination.

FIG. 17 is a flowchart illustrating the process of confirming a deficiency. First, a marker of a deficiency candidate is shown on the portion which has been determined as a deficiency in the automatic determination (171). Next, the computer 5 request an inspector to determine deficiency candidates one by one (172). The inspector determines if it is a real deficiency while viewing the color original image (173). When the inspector recognizes it as a real deficiency, the position, length, contrast and so forth of the deficiency are registered in the data memory device 7 (174) and the color of the marker is turned to red (175).

When the inspector determines the portion as a deficiency candidate in the confirmation of the deficiency candidate, the marker is erased (176). If there remains a deficiency candidate, the marker is given on the next deficiency candidate. When confirmation of all the deficiency candidates is completed (177), the color original image is saved in the data memory device 7 (178).

Figure 18:
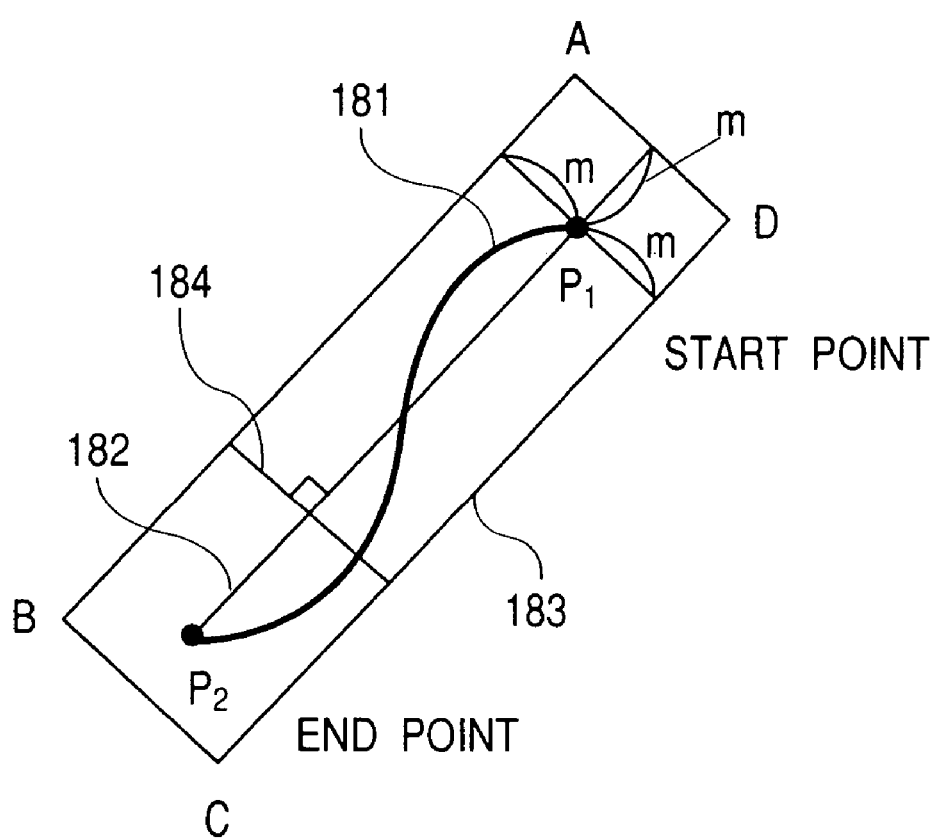
FIG. 18 is a diagram exemplifying a method of generating a deficiency candidate marker according to the invention.

FIG. 18 exemplifies a method of generating a deficiency candidate marker. A center line 182 which connects a beginning point P1 and an end point P2 of a deficiency candidate 181 is acquired, and long sides AB and CD of a deficiency candidate marker 183 are set in parallel to and apart from the center line by a given value m. Short sides AD and BC are likewise determined. The length of the deficiency is a distance between P1 and P2. In case of the magnetic-particle inspection, the contrast that is related to the depth of the deficiency is acquired by scanning a contrast computation line 184 from P1 to P2, acquiring a difference between an average luminance and a highest luminance on this line, acquiring this difference from P1 to P2, and setting an average value of the differences as the contrast of the deficiency. The deficiency candidate marker should not necessarily be rectangular. The short sides AD and BC may be made semicircles; the key point is that a deficiency should not be hidden by the marker.

Figure 19:
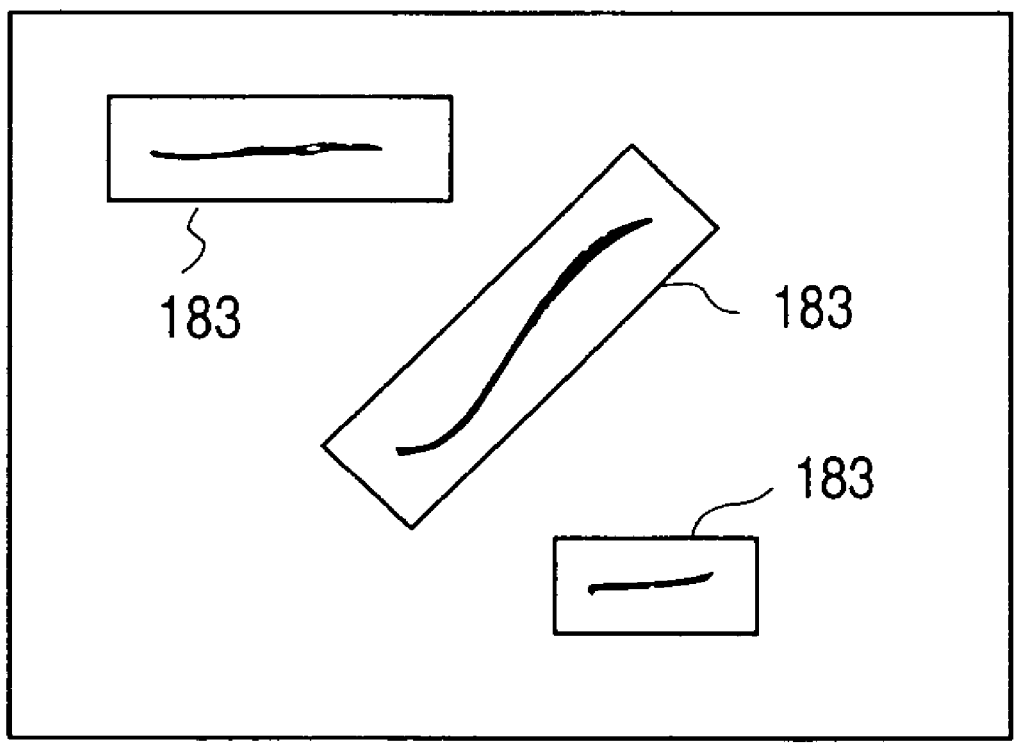
FIG. 19 is a diagram exemplifying a deficiency candidate displaying method according to the invention.

FIG. 19 exemplifies a method of displaying a deficiency candidate on the color monitor 6. The inspector is requested to confirm candidates on the original image in order from a candidate whose deficiency length is long. First, all the markers are displayed in white, the marker of the candidate which has been determined as a real deficiency is changed to another color, e.g., red, and the marker of the candidate which has been determined as a pseudo deficiency is erased.

Figure 20:
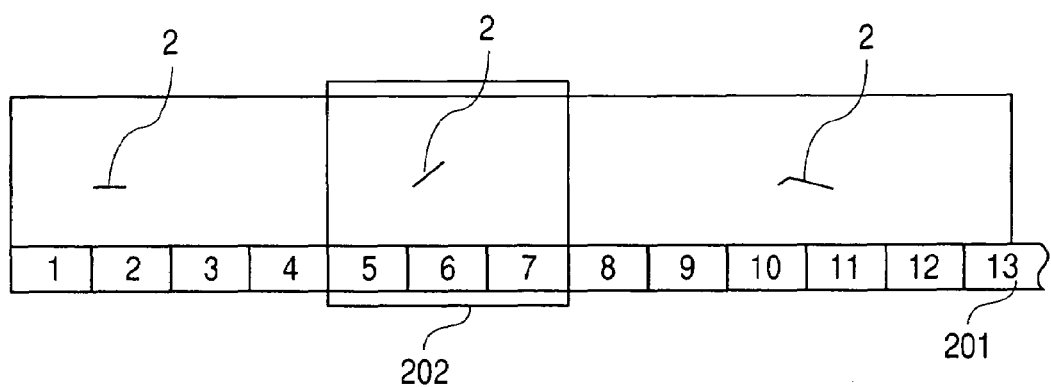
FIG. 20 is a diagram showing one example of a method of specifying an inspection position in the invention.

FIG. 20 shows one example of a method of specifying an inspection position when the specimen 1 is an elongated object. A scale 201 with graduations is fixed to the specimen 1 and image pickup is carried out in such a way that the scale 201 comes into a part of a camera's visual field 202. The graduations of the scale may be made by writing numerals, for example, every centimeter. Further, the scale 201 for the penetrant inspection may be made different in color from the scale 201 for the magnetic-particle inspection. In the magnetic-particle inspection, for example, the numerals on the scale are graduations and numerals in fluorescent green color on the white background.

Figure 21:
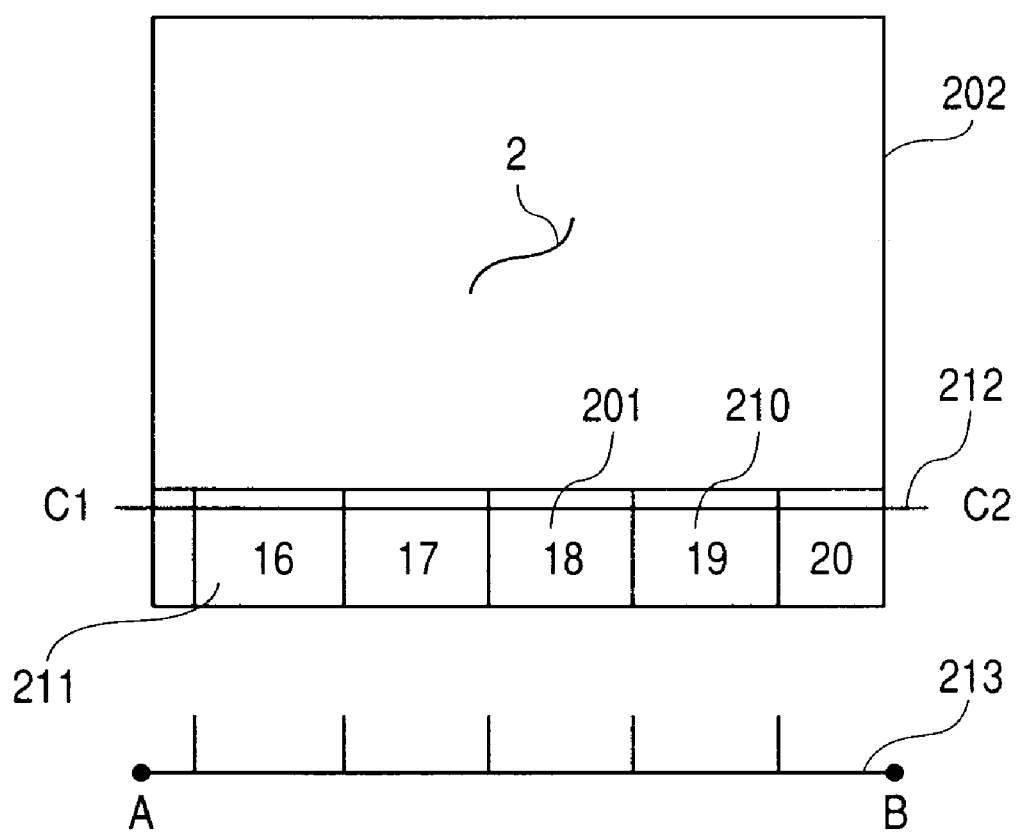
FIG. 21 is a diagram showing one example of an inspection image which contains information for specifying the inspection position in the invention.

FIG. 21 shows one example of a picked-up screen. The scale 201 is picked up at the lower portion of the screen at the same time, and the camera position on the specimen 1 is computed from the scale 201. That is, graduation numerals 210 are described on the scale 201 and can be identified by pattern matching or the like using the computer 5. The scale 201 has segmentation lines 211, for example, every centimeter, so that the finer camera position can be computed. A cross-section signal 213 is acquired as an image signal of an inspection line 212 between C1 and C2 on the image. From the signal, a left-hand end A and a right-hand end B of the image and the positions of 16-20 of the segmentation lines 211 are known. The image pickup magnification can be computed from the positions of 16-20, and the accurate position of the deficiency 2 on the specimen 1 can be known based also on the graduation numerals 210.

Figure 22:
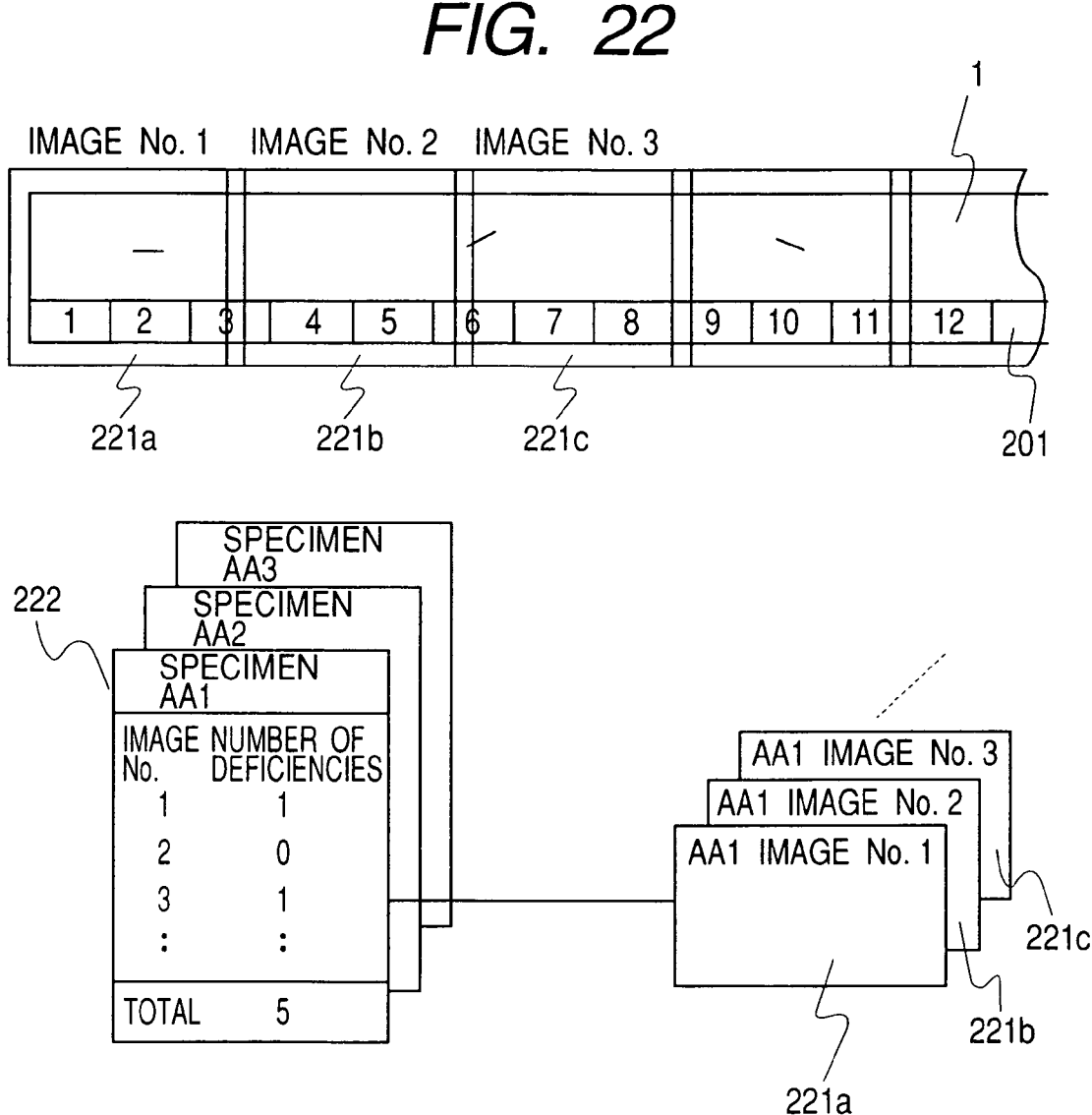
FIG. 22 is a diagram showing one example of the structure of inspection result data to be stored in a memory device 7.

The above-described inspection results are stored in the memory device 7, and an example of the storage is illustrated in FIG. 22. When the specimen 1 has a large surface to be inspected and the whole to-be-inspected surface cannot fit in a single inspection screen, it is segmented into several images before image pickup and inspection are carried out. At this time, the images to be segmented are set in such a way that the pickup ranges on the inspection surface overlap one another a little. 221a, 221b and 221c indicate image segments of the specimen 1. Inspection is performed on each image segment. The results or the entire image information for each specimen is stored together and information of each deficiency, such as the position, length, area, chromaticity and hue, is also stored as shown in 222.

The inspector first displays the data 222 for each specimen stored in the memory device 7 on the screen of the monitor 6 and checks it. When the inspector wants to see the details of the portion where a deficiency exists, he calls a corresponding image segment from the name of the specimen and the image No. and displays it on the screen of the monitor 6. At this time, information, such as the position, length, area, chromaticity and hue of a deficiency, which is stored in association with the displayed image data can also be displayed on the screen of the monitor 6.

Highlighting the detected deficiency candidate on the screen using a marker or the like can prevent overlooking of a deficiency, on the screen, which is larger than 0.1 to 0.3 mm of the same degree as that in the visual inspection done conventionally.

Further, increasing the image detection magnification can permit a deficiency smaller than a visible one to be detected. Displaying a deficiency smaller than a visible one on the screen in magnified manner can allow the position, length, area, chromaticity, hue, etc. of even a deficiency smaller than a visible one to be confirmed on the screen.

As an image is input using a color video camera according to the invention and ultraviolet rays reflected from a specimen can be cut by the ultraviolet-rays cutting filter in deficiency inspection by the magnetic-particle inspection method, an inspector can easily confirm the results of the automatic deficiency inspection. Further, because a deficiency candidate is automatically indicated and displayed on the screen, miss-inspection hardly occurs. What is more, as the inspected image is saved, it is possible to display the image saved after inspection on the screen and check a deficiency again, thus improving the inspection reliability.

As a color video camera is used in the invention, automatic deficiency inspections of the magnetic-particle inspection and penetrant inspection can be executed by the same sensor probe, so that the usability is improved considerably.

What is claimed is:

1. An inspection method, comprising:
   irradiating an ultraviolet ray on a surface of a specimen to which a solution containing fluorescent magnetic powder is applied;
   picking up an image of said surface irradiated with said ultraviolet ray by a color camera through a filter;
   processing said picked up image by using information of luminance of a green signal component which is differentiated from an RGB image output from the color camera;
   storing said processed image in a memory; and
   displaying on a screen said processed image stored in said memory,
   wherein in the picking up said image, said image of said surface is picked up by said color camera over plural visual fields.

2. An inspection method according to the claim 1, wherein said filter cuts off an ultraviolet ray reflected from said specimen, caused by the irradiating with the ultraviolet ray.

3. An inspection method according to the claim 1, wherein in the picking up of an image, an indicia which indicates a positional information of the picked-up image is included with the picked-up image.

4. An inspection method according to the claim 1, wherein in the displaying, said image displayed on the screen includes an indicia which indicates a positional information of the image.

5. An inspection method according to the claim 1, comprising:
   determining a threshold value for binarization from an average value of the differentiated said green signal component;
   performing the binarization on the processed image using the average value, to obtain a binarized image;
   removing image noise from the binarized image to obtain a de-noised image;
   determining deficiency candidates from the de-noised image; and
   determining a deficiency candidate as a deficiency, when at least one predetermined parameter of the deficiency candidate is larger than a predetermined value.

6. An inspection apparatus, comprising:
   ultraviolet ray irradiation means for irradiating an ultraviolet ray on a surface of a specimen to which a solution containing fluorescent magnetic powder is applied;
   image pick up means for picking up an image of said surface irradiated with said ultraviolet ray by a color camera through a filter;
   image processing means for processing said picked up image by using information of luminance of a green signal component which is differentiated from an RGB image output from the color camera;
   memory means for storing said image processed by said image processing means; and display means for displaying on a screen said image stored in said memory, wherein said image pick up means picked up said image of said surface by said color camera over plural visual fields.

7. An inspection apparatus according to the claim 6, wherein said filter of said image pick up means cuts off an ultraviolet ray reflected from said specimen, caused by the irradiating with the ultraviolet ray irradiation means.

8. An inspection apparatus according to the claim 6, wherein said image of said surface picked up by said image pick up means includes an image of an indicia which indicates a positional information of the picked up image of said surface.

9. An inspection apparatus according to the claim 6, wherein said image displayed on the screen of said display means includes an indicia which indicates a position information of the displayed image.

10. An inspection apparatus according to the claim 6, comprising:
a threshold-determining unit adapted to determine a threshold value for binarization from an average value of the differentiated said green signal component;
a binarization unit adapted to perform the binarization on the processed image using the average value, to obtain a binarized image;
a de-noising unit adapted to remove image noise from the binarized image to obtain a de-noised image;
a candidate-determining unit adapted to determine deficiency candidates from the de-noised image; and
a deficiency-determining unit adapted to determine a deficiency candidate as a deficiency, when at least one predetermined parameter of the deficiency candidate is larger than a predetermined value.

11. An inspection method, comprising:
irradiating an ultraviolet ray on a surface of a specimen to which a solution containing fluorescent magnetic powder is applied;
picking up an image of said surface irradiated with said ultraviolet ray by a color camera;
processing said picked up image by separating a green signal component from an image output of the color camera, and mathematically differentiating the separated said green signal component to obtain a processed image;
storing said processed image in a memory; and
displaying on a screen said processed image stored in said memory,
wherein in the picking up said image, said image of said surface is picked up by said color camera over plural visual fields.

12. An inspection method according to the claim 11, comprising a filter which cuts off an ultraviolet ray reflected from said specimen, caused by the irradiating with the ultraviolet ray.

13. An inspection method according to the claim 11, wherein in the picking up of an image, an indicia which indicates a positional information of the picked-up image is included with the picked-up image.

14. An inspection method according to the claim 11, wherein in the displaying, said image displayed on the screen includes an indicia which indicates a positional information of the image.

15. An inspection method according to the claim 11, comprising:
determining a threshold value for binarization from an average value of the differentiated said green signal component;
performing the binarization on the processed image using the average value, to obtain a binarized image;
removing image noise from the binarized image to obtain a de-noised image;
determining deficiency candidates from the de-noised image; and
determining a deficiency candidate as a deficiency, when at least one predetermined parameter of the deficiency candidate is larger than a predetermined value.

16. An inspection apparatus, comprising:
ultraviolet ray irradiation means for irradiating an ultraviolet ray on a surface of a specimen to which a solution containing fluorescent magnetic powder is applied;
image pick up means for picking up an image of said surface irradiated with said ultraviolet ray by a color camera through a filter;
image processing means for processing said picked up image by separating a green signal component from an image output of the color camera, and mathematically differentiating the separated said green signal component to obtain a processed image;
memory means for storing said processed image from said image processing means; and
display means for displaying on a screen said processed image stored in said memory,
wherein said image pick up means picked up said image of said surface by said color camera over plural visual fields.

17. An inspection apparatus according to the claim 16, comprising a filter of said image pick up means, which cuts off an ultraviolet ray reflected from said specimen, caused by the irradiating with the ultraviolet ray irradiation means.

18. An inspection apparatus according to the claim 16, wherein said image of said surface picked up by said image pick up means includes an image of an indicia which indicates a positional information of the picked up image of said surface.

19. An inspection apparatus according to the claim 16, wherein said image displayed on the screen of said display means includes an indicia which indicates a position information of the displayed image.

20. An inspection apparatus according to the claim 16, comprising:
a threshold-determining unit adapted to determine a threshold value for binarization from an average value of the differentiated said green signal component;
a binarization unit adapted to perform the binarization on the processed image using the average value, to obtain a binarized image;
a de-noising unit adapted to remove image noise from the binarized image to obtain a de-noised image;
a candidate-determining unit adapted to determine deficiency candidates from the de-noised image; and
a deficiency-determining unit adapted to determine a deficiency candidate as a deficiency, when at least one predetermined parameter of the deficiency candidate is larger than a predetermined value.

* * * * *